United States Patent [19]

Tanaka et al.

[11] Patent Number: 4,910,350

[45] Date of Patent: Mar. 20, 1990

[54] FLUORINE-SUBSTITUTED CYCLOHEXYLCYCLOHEXENE DERIVATIVE

[75] Inventors: Yasuyuki Tanaka; Haruyoshi Takatsu; Kiyohumi Takeuchi, all of Tokyo; Yuuji Tamura, Saitama, all of Japan

[73] Assignee: Dainippon Ink and Chemicals, Inc., Tokyo, Japan

[21] Appl. No.: 250,283

[22] Filed: Sep. 28, 1988

[30] Foreign Application Priority Data

Sep. 29, 1987 [JP] Japan .................................. 62-245240
Oct. 20, 1987 [JP] Japan .................................. 62-264532

[51] Int. Cl.⁴ .................... C07C 25/18; C09K 19/30
[52] U.S. Cl. .......................... 570/129; 252/299.63; 549/16; 549/17; 549/31; 549/336
[58] Field of Search ............................................ 570/129

[56] References Cited

U.S. PATENT DOCUMENTS 4,405,488  9/1983  Sugimori et al. .................. 570/126

FOREIGN PATENT DOCUMENTS 3317921 12/1983  Fed. Rep. of Germany ...... 570/129
0004929  1/1982  Japan .................................. 570/129
0198427 11/1983  Japan .................................. 570/129
0198428 11/1983  Japan .................................. 570/129
0016841  1/1984  Japan .................................. 570/129
0082323  5/1984  Japan .................................. 570/129

Primary Examiner—J. E. Evans
Attorney, Agent, or Firm—Armstrong, Nikaido, Marmelstein, Kubovcik & Murray

[57] ABSTRACT

A compound represented by formula (I):

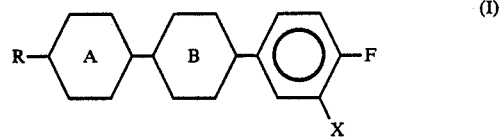

wherein R represents a straight chain alkyl group having from 1 to 9 carbon atoms;

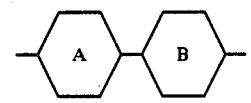

represents

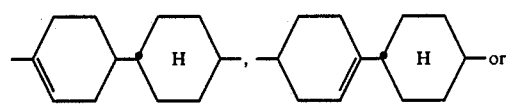

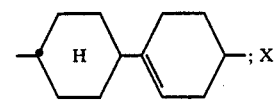

represents a hydrogen atom or a fluorine atom; and

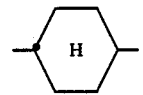

has a trans (equatorial-equatorial) configuration, is disclosed. The compound of formula (I) exhibits a nematic phase in the vicinity of room temperature or in a temperature range higher than room temperature and has a small optical anisotropy and a positive dielectric anisotropy and is, therefore, useful in preparing a liquid crystal display cell excellent in viewing-angle characteristics.

21 Claims, No Drawings

FLUORINE-SUBSTITUTED CYCLOHEXYLCYCLOHEXENE DERIVATIVE

FIELD OF THE INVENTION

This invention relates to a fluorine-substituted cyclohexylcyclohexene derivative useful as an electrooptical display material and an intermediate thereof and processes for preparing the same.

BACKGROUND OF THE INVENTION

Typical liquid crystal display cells heretofore developed include a field effect mode cell proposed by M. Schadt et al., *Applied Physics Letters*, Vol. 18, 127-128 (1971), a dynamic scattering mode cell proposed by G. H. Heilmeier et al., *Proceeding of the I.E.E.E.*, Vol. 56, 1162-1171 (1968), and a guest-host cell proposed by G. H. Heilmeier, et al., *Applied Physics Letters*, Vol. 13, 91 (1968) and D. L. White et al., *Journal of Appleid Physics*, Vol. 45, 4718 (1974).

The most current of these liquid crystal display cells is a twisted nematic code cell (TN cell), a kind of the field effect mode cells. As reported by G. Bauer, *Mol. Cryst. Liq. Cryst.*, Vol. 63, 45 (1981), the TN cell requires that a product of an optical anisotropy ($\Delta n$) of a liquid crystal material filled in the cell and a thickness (d)$\mu$m of a liquid crystal layer in the cell should be set at a certain specific value in order to prevent generation of an interference fringe on the cell surface which would impair the cell appearance. In the liquid crystal cells for practical use, the abovedescribed product $\Delta n \cdot d$ is set at 0.5, 1.0, 1.6, or 2.2. In general, setting of the $\Delta n \cdot d$ value at 0.5 brings about satisfactory viewing-angle characteristics, and setting at 1.0, 1.6, or 2.2 brings about an improved contrast when seen from the front. Therefore, it is usual to set the $\Delta n \cdot d$ value at 0.5 in cases where a liquid crystal display cell is demanded to be easy to see from any direction, while, in cases where the cell is demanded to show a contrast from the front, the $\Delta n \cdot d$ value is set at 1.0, 1.6, or 2.2.

On the other hand, since the thickness of the liquid crystal layer in the currently employed cells is usually selected from a limited range of from 6 to 10 $\mu$m, setting of the $\Delta n \cdot d$ at 0.5 naturally needs a liquid crystal material having a small $\Delta n$, while setting at 1.0 needs a liquid crystal material having a large $\Delta n$. Hence, whether a liquid crystal material should have a small $\Delta n$ or a large $\Delta n$ depends on the desired display characteristics of a liquid crystal display cell.

Most of the practical liquid crystal materials are generally prepared by mixing several kinds of compounds exhibiting a nematic phase in the vicinity of room temperature and compounds exhibiting a nematic phase at temperatures higher than room temperature. Since these mixed liquid crystals for practical use are required, in many cases, to exhibit a nematic phase at least over the entire temperature range of from $-30°$ C. to $+65°$ C., compounds having a nematic phase in the vicinity of room temperature or in the temperature range higher than room temperature are needed.

Further, the mixed liquid crystals in the TN cell should have positive dielectric anisotropy ($\Delta \epsilon$), thus needing those nematic liquid crystal compounds whose value is positive.

SUMMARY OF THE INVENTION

One object of this invention is to provide a novel liquid crystal compound exhibiting a nematic phase at around room temperature or in a temperature range higher than room temperature and having a small $\Delta n$ and a positive $\Delta \epsilon$.

The present invention relates to a compound represented by formula (I):

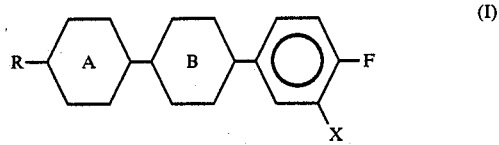

wherein R represents a straight chain alkyl group having from 1 to 9 carbon atoms;

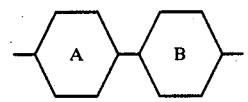

represents

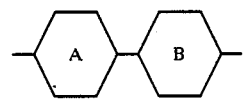

represents a hydrogen atom or a fluorine atom; and

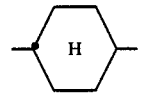

has a trans (equatorial-equatorial) configuration.

DETAILED DESCRIPTION OF THE INVENTION

The compound represented by formula (I) can be synthetized according to the following reaction scheme A or B:

Scheme A:

Synthesis of Compounds (I) wherein

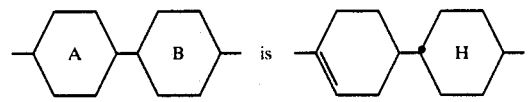

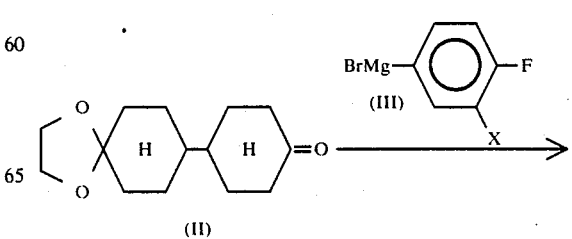

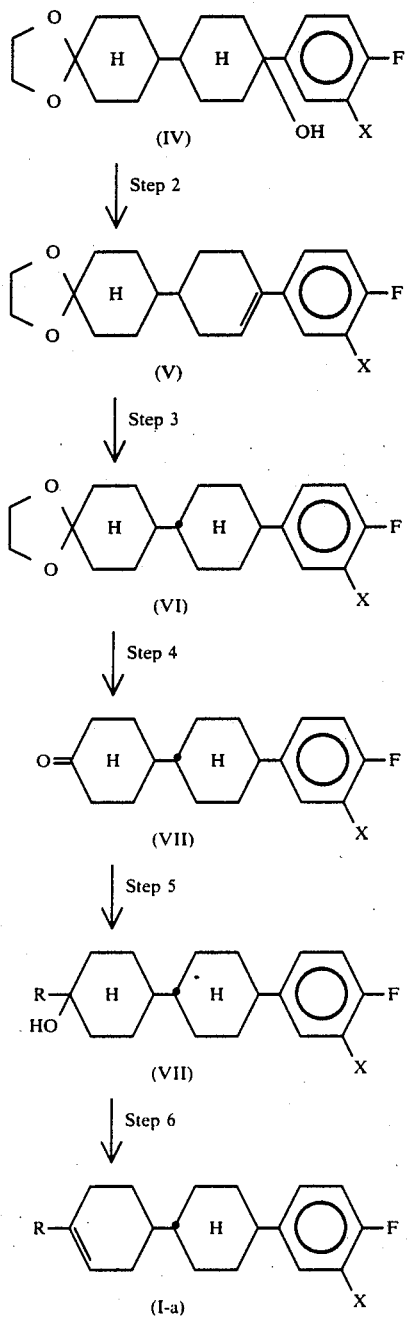

wherein R and X are as defined above.

Step 1

A compound of formula (II) is reacted with a Grignard reagent of formula (III) in an ether solvent, e.g., anhydrous diethyl ether or anhydrous tetrahydrofuran (THF). After completion of the reaction, dilute hydrochloric acid is added dropwise to the reaction mixture to effect hydrolysis. The reaction product is extracted with an inert solvent, e.g., benzene or toluene, washed with water, and dried. The solvent is removed from the extract by distillation under reduced pressure to obtain a compound of formula (IV).

Step 2

The compound of formula (IV) is dehydrated in an inert solvent, e.g., benzene or toluene, in the presence of p-toluenesulfonic acid. The product is washed with water, dried, and distilled under reduced pressure to remove the solvent. Recrystallization from ethanol yields a compound of formula (V).

Step 3

The compound of formula (V) is reduced in a mixed solvent of ethanol and n-hexane in the presence of Raney nickel as a catalyst. The reaction product is filtered to remove the catalyst, and the solvent is removed from the filtrate by distillation under reduced pressure. Recrystallization from ethanol gives a compound of formula (VI).

Step 4

The compound of formula (VI) is dissolved in an inert solvent, e.g., benzene or toluene, and the solution is hydrolyzed with a strong acid, e.g., hydrochloric acid or sulfuric acid. The reaction mixture is washed with water and dried. The solvent was removed by distillation under reduced pressure to obtain a compound of formula (VII).

Step 5

The compound of formula (VII) is reacted with an n-alkylmagnesium bromide in an ether solvent, e.g., anhydrous diethyl ether or anhydrous THF. After completion of the reaction, dilute hydrochloric acid is added dropwise to the reaction mixture to effect hydrolysis. The reaction mixture is extracted with an inert solvent, e.g., benzene or toluene, washed with water, and dried. The solvent is removed from the extract by distillation under reduced pressure to obtain a compound of formula (VIII).

Step 6

The compound of formula (VIII) is dehydrated in an inert solvent, e.g., benzene or toluene, in the presence of p-toluenesulfonic acid. The reaction product is washed with water and dried. The solvent is removed therefrom by distillation under reduced pressure. Recrystallization from ethanol gives the entitled compound of formula (I-a).

Scheme B

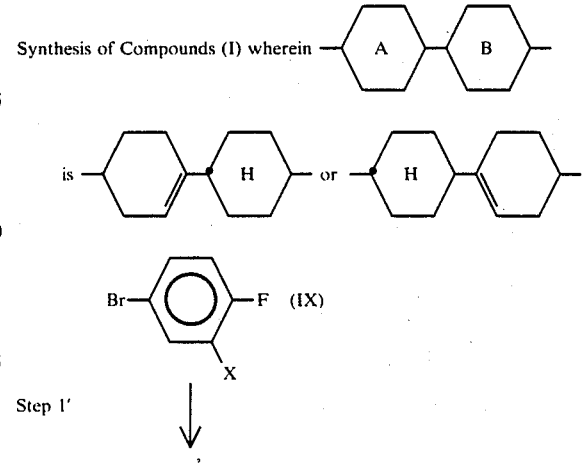

Step 1'

Synthesis of Compounds (I) wherein 

is 

Step 2'

Step 3'

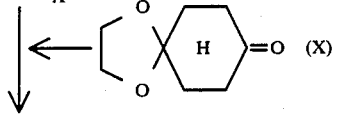

Step 4'

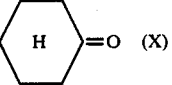

Step 5'

Step 6'

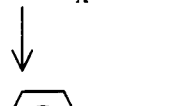

Step 7'

+

Synthesis of Compounds (I) wherein 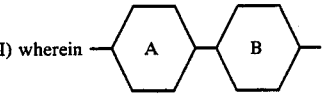

is 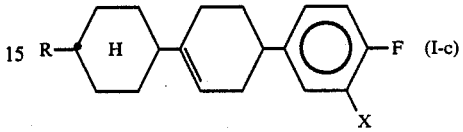

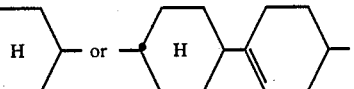

wherein R and X are as defined above.

Step 1'

A compound of formula (IX) is reacted with a metallic magnesium powder in an ether solvent, e.g., anhydrous THF, at 20° to 30° C. for 1 to 2 hours to prepare a compound of formula (III).

Step 2'

To a solution of the compound of formula (III) is added an anhydrous THF solution of a compound of formula (X) at 5° to 20° C., followed by allowing the mixture to react at 10° to 30° C. for 30 minutes. The reaction product is decomposed with a saturated aqueous solution of ammonium chloride to obtain a compound of formula (XI).

Step 3'

The compound of formula (XI) is refluxed in an inert water insoluble solvent, e.g., toluene, in the presence of an acidic catalyst, e.g., p-toluenesulfonic acid, for 2 to 8 hours. After cooling the reaction mixture, the organic solvent layer is washed successively with a saturated aqueous solution of sodium carbonate and a saturated sodium chloride aqueous solution and dried. The organic solvent is then removed by distillation. The resulting crude product is recrystallized from an alcohol solvent, e.g., methanol, to obtain a compound of formula (XII).

Step 4'

The compound of formula (XII) is catalytically reduced in an alcohol solvent, e.g., ethanol, in the presence of a hydrogenating catalyst, e.g., Raney nickel, under a hydrogen pressure of not higher than 3 kg/cm² at room temperature for 6 to 20 hours to prepare a compound of formula (XIII).

Step 5'

The compound of formula (XIII) is reacted with an acidic aqueous solution, e.g., dilute hydrochloric aicd, in an inert organic solvent, e.g., toluene, at reflux for 4 hours. The reaction mixture is cooled, and the organic solvent layer is washed with water and dried. The organic solvent is removed from the solution by distillation. The resulting crude product is recrystallized from n-hexane to obtain a compound of formula (XIV).

Step 6'

A compound of formula (XV) is reacted with lithium in an ether solvent, e.g., anhydrous diethyl ether, at reflux for 2 to 8 hours to form a lithium salt. To the reaction mixture is added a solution of the compound of formula (XIV) in an ether solvent, e.g., anhydrous diethyl ether, at 0° to 15° C., and the mixture is allowed to react at 5° to 20° C. for 30 minutes. Water is added to the reaction mixture to perform hydrolysis. The reaction product is extracted with toluene, and the extract is washed with water and dried. The solvent is removed from the extract by distillation to obtain a compound of formula (XVI).

Step 7'

The compound of formula (XVI) is dissolved in n-hexane, and the solution is added to an acetonitrile solution of iodotrimethylsilane prepared by reacting chlorotrimethylsilane and sodium iodide in acetonitrile, and the mixture is allowed to react at 5° to 10° C. for 30 minutes. To the reaction mixture is then added a base, e.g., 1,8-diaza-bicyclo(5,4,0)undecene-7 (DBU), followed by allowing to react at 5° to 30° C. for 5 to 20 hours. Water is added to the reaction mixture, and the reaction product is extracted with toluene. The extract is washed successively with dilute hydrochloric acid, a saturated sodium hydrogencarbonate aqueous solution, and a saturated sodium chloride aqueous solution, followed by drying. The solvent is removed from the extract by distillation. The crude reaction product is refluxed in a solvent, e.g., toluene, in the presence of an acidic catalyst, e.g., p-toluenesulfonic acid, for 1 to 8 hours to thereby isomerize the cyclohexane ring from a cis-configuration to a trans-configuration. Thus, there is obtained a mixture of a compound of formula (I-b) and a compound of formula (I-c) in good yield. After completion of the reaction, the toluene layer is washed successively with a saturated sodium hydrogencarbonate aqueous solution and a saturated sodium chloride aqueous solution, followed by drying. The toluene is removed from the extract by distillation. The crude reaction product is purified by silica gel column chromatography and then recrystallized from ethanol. The recrystallized mixture is separated into each component by liquid chromatography, and each of the thus separated compounds is recrystallized from ethanol to obtain the compound of formula (I-b) and the compound of formula (I-c).

The dicyclohexyl-4,4'-dione monoketal derivative represented by formula (II) is a novel compound.

The comound of formula (II) can be prepared according to the following reaction scheme:

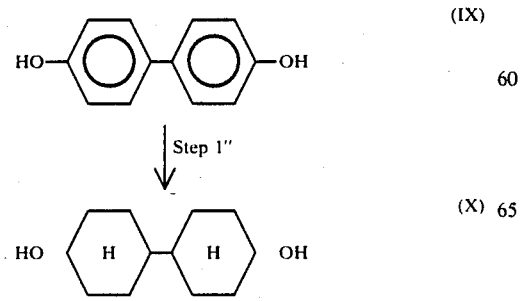

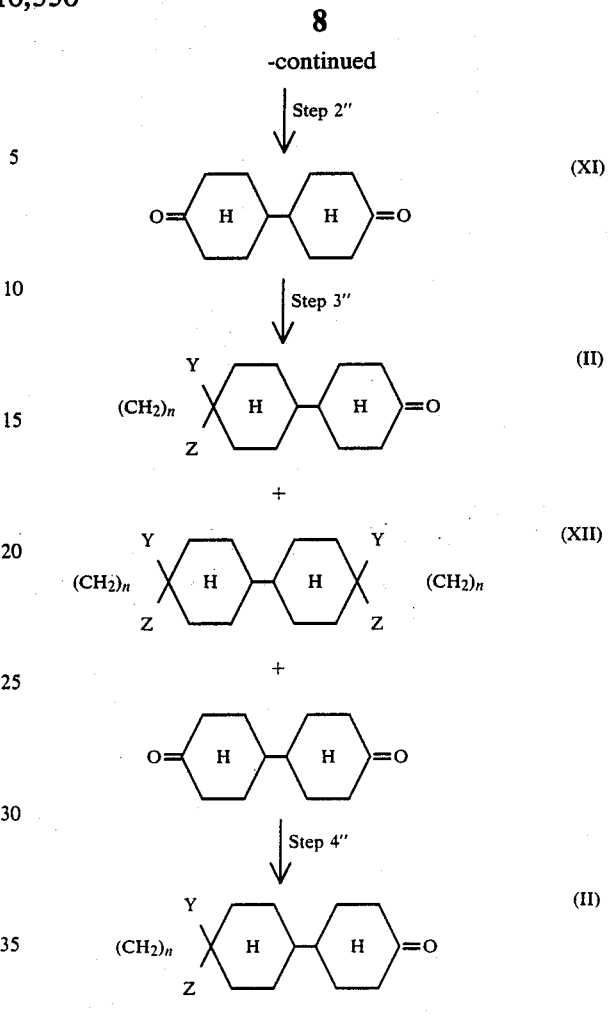

Step 1"

Biphenyl-4,4'-diol of formula (IX) is dissolved in an alcohol (e.g., ethanol, isopropanol) and reduced in the presence of anhydrous sodium carbonate using 5 wt% palladium-on-carbon as a reducing catalyst under a medium pressure to prepaer dicyclohexyl-4,4'-diol of formula (X).

Step 2"

The compound of formula (X) obtained in Step 1" is dissolved in a non-polar organic solvent (e.g., toluene) and oxidized with an oxidizing agent (e.g., chromic acid) to prepare dicyclohexyl-4,4'-dione of formula (XI).

Step 3"

The compound of formula (XI) obtained in Step 2" is dissolved in a non-polar solvent (e.g., benzene, toluene) and subjected to dehydrating condensation with a ketal agent (e.g., ethylene glycol, 2-mercaptoethanol, 1,2-ethanedithiol) in the presence of an acidic catalyst (e.g., potassium hydrogensulfate) to prepare a reaction mixture containing compounds of formulae (II), (XI), and (XII).

Step 4"

The reaction mixture obtained in Step 3" is reacted with sodium hydrogensulfite in a two-phase system of water and toluene to form a sodium hydrogensulfite salt of the compound of formula (XI), which is removed by filtration. The organic layer separated from the filtrate is concentrated to dryenss under reduced pressure, and the residue is dissolved in a polar organic solvent (e.g., ethyl acetate). The solution is treated with a sodium hydrogensulfite aqueous solution having a high concentration to form a salt of the compound of formula (II), followed by filtration. The collected crystals are treated with aqueous ammonia to form the compound of formula (II), extracted with toluene and washed with water. The solvent is removed by distillation under reduced pressure. The resulting extract is purified, for example, by recrystallization to prepare the compound of formula (II).

Transition temperatures of typical compounds of formula (I) are listed in Table 1 below.

TABLE 1

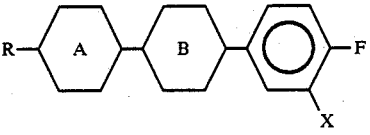

| Compound No. | R | A–B | X | Transition Temperature (°C.) |
|---|---|---|---|---|
| 1 | n-C₃H₇— | 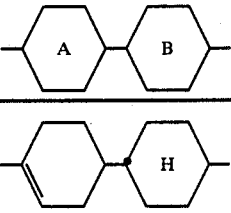 | H | 76 (C → N)<br>95 (N ⇌ I) |
| 2 | n-C₃H₇— | 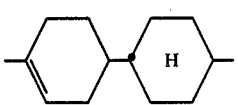 | F | 19 (C → N)<br>53 (N ⇌ I) |
| 3 | n-C₅H₁₁— | 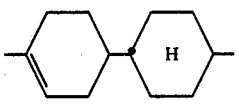 | F | −6 (C → N)<br>43 (N ⇌ I) |
| 4 | n-C₃H₇— | 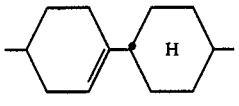 | H | 56 (C → N)<br>97 (N ⇌ I) |
| 5 | n-C₃H₇— | 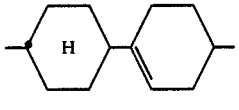 | H | 45 (C → N)<br>91 (N ⇌ I) |
| 6 | n-C₃H₇— | 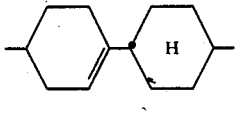 | F | 23 (C → N)<br>59 (N ⇌ I) |
| 7 | n-C₃H₇— | 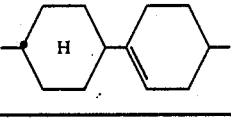 | F | 23 (C → N)<br>55 (N ⇌ I) |

Note:
In Table 1, C represents a crystalline phase; N represents a nematic phase; and I represents an isotropic liquid phase.

The compounds of formula (I) according to the present invention are nematic liquid crystal compounds having positive dielectric anisotropy. They can be used in dynamic scattering mode cells in the form of a mixture with other nematic liquid crystal compounds having negative dielectric anisotropy, or in field effect mode cells in the form of a mixture with other nematic liquid crystal compounds having positive or negative dielectric anisotropy.

Typical examples of compounds which can preferably be mixed with the compounds of the present invention to the above-described utility are 4-substituted benzoic acid 4′-substituted phenyl ester, 4-substituted cyclohexanecarboxylic acid 4'-substituted phenyl ester, 4-substituted cyclohexanecarboxylic acid 4'-substituted biphenyl ester, 4-(4-substituted cyclohexanecarbonyloxy)benzoic acid 4'-substituted phenyl ester, 4-(4-substituted cyclohexyl)benzoic acid 4'-substituted phenyl ester, 4-(4-substituted cyclohexyl)benzoic acid 4'-substituted cyclohexyl ester, 4,4'-disubstituted biphenyl, 4-substituted phenyl-4'-substituted-cyclohexane, substituted terphenyl, 4-substituted biphenyl-4'-substituted cyclohexane, 2-(4-substituted phenyl)-5-substituted pyrimidine, etc.

Compound Nos. 2, 3, 6 and 7 having a formula (I) of the present invention shows a nematic phase at room temperature, and their physical properties are as shown in Table 2.

TABLE 2

|  | Compound No. | | | |
| --- | --- | --- | --- | --- |
|  | 2 | 3 | 6 | 7 |
| Δn (—) | 0.0730 | 0.0634 | 0.0780 | 0.0750 |
| Threshold Voltage (V) | 1.87 | 1.68 | 1.95 | 1.91 |
| Δε (—) | 5.0 | 3.85 | 5.6 | 5.6 |

A mixture consisting of 40% by weight of Compound No. 1, 30% by weight of Compound No. 2, and 30% by weight of Compound No. 3 shows a nematic phase at a temperature between 0° C. and 66° C. and has a Δn of 0.0813, a threshold voltage of 2.25 V, and a Δε of 4.51.

A mixture consisting of 50% by weight of Compound No. 5 and 50% by weight of Compound No. 7 exhibits a nematic phase at a temperature between 26° C. and 73° C. and has a Δn of 0.082 and a Δε of 4.6 as measured at room temperature in a supercooled state.

It can be understood from these results that the compounds of the present invention exhibit a nematic phase at around room temperature or at a temperature higher than room temperature and has a small Δn value and a positive Δε value and are, therefore, suitable in preparing nematic liquid crystal display cells having excellent viewing-angle characteristics.

As described above, the compounds of formula (I) according to the present invention exhibit a nematic phase in the vicinity of room temperatures or in a temperature range higher than room temperature and has an extremely small optical anisotropy Δn with a positive dielectric anisotropy Δε. Therefore, these compounds are very useful as materials for preparing liquid crystal display cells excellent in viewing-angle characteristics.

The present invention is now illustrated in greater detail by way of the following Examples, but it should be understood that the present invention is not deemed to be limited thereto. In these examples, all the percents and ratios are given by weight unless otherwise indicated.

EXAMPLE 1

In 1 l of isopropanol was dissolved 100 g (0.54 mol) of biphenyl-4,4'-diol, and 5 g of anhydrous sodium carbonate and 5 g of 5% palladium-on-carbon were added to the solution. The mixture was subjected to reduction reaction in an autoclave at 100° C. and at a hydrogen pressure of 5 kg/cm² for 25 to 30 hours. After completion of the reaction, the reaction mixture was filtered, and the isopropanol was removed from the filtrate by distillation under reduced pressure to recover a part of dicyclohexyl-4,4'-diol. The crystals obtained as a filter cake were dissolved in 500 ml of tetrahydrofuran while hot and filtered. The tetrahydrofuran was removed from the filtrate by distillation under reduced pressure to obtain dicyclohexyl-4,4'-diol. Both crystals were combined, suspended in 1 l of n-hexane while hot, and allowed to stand at 5° to 6° C. for 1 hour. The precipitated crystals were collected by filtration and dried under reduced pressure to obtain 93 g (0.47 mol) of a compound of formula:

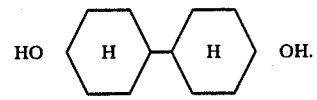

Melting Point: 179°–181° C.

In 460 ml of toluene was dissolved 93 g (0.47 mol) of the compound, and to the solution was added dropwise a mixture which comprises 138 g (0.46 mol) of sodium chromate dihydrate, 525 ml of water, 184 ml of sulfuric acid, and 55 ml of acetic acid, over a period of 2 hours while maintaining the solution at 40° C. or lower by stirring under water-cooling. After the dropwise addition, the mixture was allowed to further react at that temperature for 2 hours, and an organic layer was separated from the reaction mixture. To the aqueous layer wa added 1 l of a saturated sodium chloride aqueous solution to effect salting out, followed by extracting twice with 300 ml portions of toluene. The organic layers were combined and washed with a saturated sodium chloride aqueous solution until the washing became neutral. Then, the organic layer was dried over anhydrous sodium sulfate and distilled under reduced pressure to remove the toluene. The residue was recrystallized from a mixed solvent of 500 ml of n-hexane and 100 ml of ethyl acetate to obtain 68 g (0.35 mol) of a compound of formula:

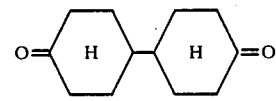

Melting Point: 117°–118° C.

To 340 ml of toluene were added 68 g (0.35 mol) of the resulting product, 26.2 g (0.42 mol) of ethylene glycol, and 130 mg of potassium hydrogensulfate. The mixture was heat-refluxed in a reaction vessel equipped with a water separator while removing produced water out of the reaction system. After completion of the reaction, the reaction mixture was allowed to cool to room temperature. As a result of gas chromatography, the reaction mixture was found to be a mixture comprising compound of formulae:

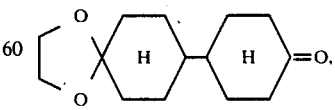

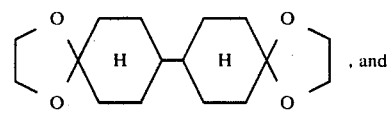, and

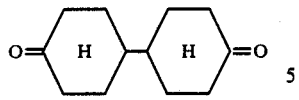

at a weight ratio of 13:51:36.

To the reaction mixture was added a solution of 14.3 g (0.14 mol) of sodium hydrogensulfite in 290 ml of water, followed by stirring for 30 minutes. The thus precipitated sodium hydrogensulfite of a compound of formula:

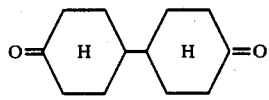

was separated by filtration. The filtrate was separated into an aqueous layer and an organic layer, and the organic layer was distilled under reduced pressure to remove toluene. The residue was dissolved in 400 ml of ethyl acetate. To the solution was again added a solution of 70 g (0.67 mol) of sodium hydrogensulfite in 250 ml of water, followed by stirring for 30 minutes. The thus precipitated sodium hydrogensulfite of a compound of formula:

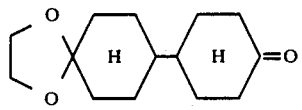

was collected by filtration, washed two or three times with 200 ml portions of ethyl acetate, and poured into a large quantity of 10% aqueous ammonia, followed by stirring for 30 minutes. The reaction mixture was extracted twice with 200 ml portions of toluene, and the organic layer was washed successively with a 5% sodium hydrogensulfite aqueous solution and water and dried over anhydrous sodium sulfate. The solvent was removed by distillation under reduced pressure. The residue was recrystallized from a mixed solvent of 500 ml of n-hexane and 100 ml of ethyl acetate to obtain 28.4 g of a compound of formula:

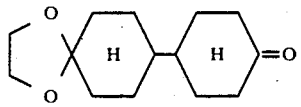

Yield: 34%
Melting Point: 109° C.

EXAMPLE 2

In 80 ml of anhydrous THF was dissolved 17.5 g (0.100 mol) of p-bromofluorobenzene, and the solution was added dropwise to 2.67 g (0.110 gram atom) of a metallic magnesium powder at 30° to 40° C. while stirring. The mixture was allowed to react at room temperature for an additional period of 2 hours to form p-fluorophenylmagnesium bromide.

In 80 ml of anhydrous THF was dissolved 21.4 g (0.0899 mol) of a compound of Example 1 having formula:

and the solution was added dropwise to the above-prepared Grignard reagent at 15° to 20° C. while stirring, and the mixture was allowed to further react at room temperature for 1 hour. After completion of the reaction, 100 ml of 2% dilute hydrochloric acid was slowly added dropwise to the reaction mixture while cooling. The reaction mixture was then extracted with toluene, and the extract was washed with water until the washing became neutral. Anhydrous sodium sulfate was added to the extract to dry it, followed by filtration. The solvent was removed from the filtrate by distillation under reduced pressure to obtain a crude product of formula:

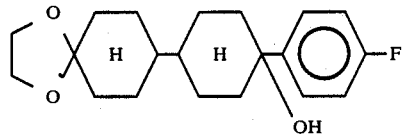

The crude product was dissolved in 150 ml of toluene, and 0.5 g of p-toluenesulfonic acid monohydrate was added to the solution. The mixture was refluxed under stirring for 2 hours while removing the produced water by decantation. The reaction mixture was cooled, and the toluene layer was washed with water, dried over anhydrous sodium sulfate, and distilled to remove the toluene. The resulting product was recrystallized from ethanol to obtain 18.5 g (0.0585 mol) of a compound of formula:

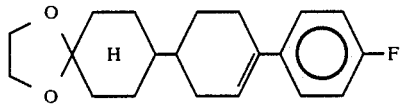

The thus prepared compound was dissolved in a mixed solvent of 90 ml of ethanol and 90 ml of ethyl acetate and subjected to reduction using 2 g of Raney nickel as a catalyst under a hydrogen pressure of 3 kg/m². After the reaction, Raney nickel was separated by filtration, and the solvent was removed from the filtrate by distillation to obtain a crude product of formula:

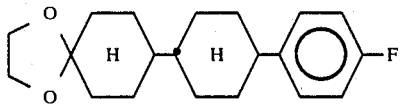

The crude product was dissolved in 80 ml of toluene, and 50 ml of 25% sulfuric acid was added thereto, followed by stirring at 60° C. for 3 hours. After cooling, the toluene layer was washed with water and dried over anhydrous sodium sulfate. The toluene was removed by distillation. Recrystallization of the resulting crude product yielded 9.74 g (0.0355 mol) of a compound of the following formula (melting point: 92° C.):

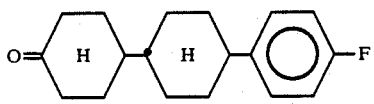

In 20 ml of anhydrous THF was dissolved 4.80 g (0.0390 mol) of n-propyl bromide, and the solution was added dropwise to 1.04 g (0.0428 mol) of a metallic magnesium powder at 30° to 40° C. while stirring, followed by allowing the mixture to react at room temperature for 2 hours to prepare a Grignard reagent. To the reaction mixture was added dropwise a solution of 9.74 g (0.0355 mol) of the above-prepared compound of formula:

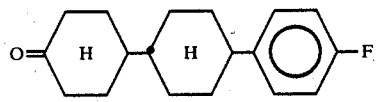

in 20 ml of anhydrous THF at 15° to 20° C. while stirring, and the reaction was further continued at room temperature for 1 hour. After completion of the reaction, 40 ml of 2% dilute hydrochloric acid was slowly added dropwise to the reaction mixture while cooling. The reaction mixture was extracted with toluene, and the extract was washed with water until the washing became neutral, and dried over anhydrous sodium sulfate. The solvent was removed therefrom by distillation to obtain a crude product of formula:

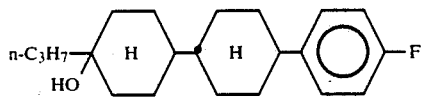

The resulting crude product was dissolved in 100 ml of toluene, and 0.2 g of p-toluenesulfonic acid monohydrate was added to the solution. The solution was refluxed under stirring while removing the produced water by decantation. After effecting the dehydration reaction for 2 hours, the reaction mixture was cooled, and the toluene layer was washed with water and dried over anhydrous sodium sulfate. The toluene was removed by distillation, and the resulting crude product was recrystallized from ethanol to obtain 6.25 g (0.0284 mol) of a compound of formula:

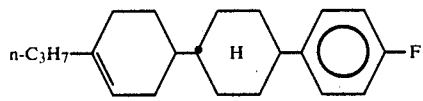

Yield: 31.6%
Transition Temperature: 76° C. (C→N); 95° C. (N⇌I)

EXAMPLE 3

A compound of the following formula was obtained in the same manner as in Example 2, except for replacing the p-bromofluorobenzene with 19.3 g (0.100 mol) of 3,4-difluorobromobenzene.

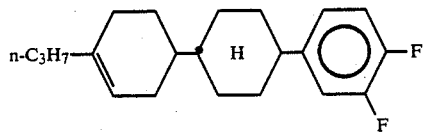

Yield: 20.6%
Transition Temperature: 19° C. (C→N); 53° C. (N⇌I)

EXAMPLE 4

A compound of the following formula was obtained in the same manner as in Example 2, except for using 19.3 g (0.100 mol) of 3,4-difluorobromobenzene in place of the p-bromofluorobenzene and using n-pentyl bromide in place of the n-propyl bromide.

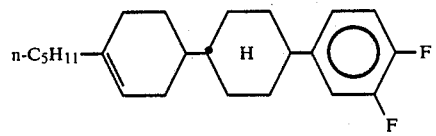

Yield: 18.7%
Transition Temperature: −6° C. (C→N); 43° C. (N⇌I)

EXAMPLE 5

In 120 ml of anhydrous THF was dissolved 29.2 g (0.167 mol) of p-bromofluorobenzene. The solution was added dropwise to 4.46 g (0.184 gram atom) of a metallic magnesium powder at 20° to 30° C. while stirring, and the reaction was further continued at room temperature (25° C.) for 2 hours to obtain a compound of formula:

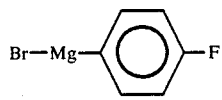

In 40 ml of anhydrous THF was dissolved 20.0 g (0.128 mol) of a compound of formula:

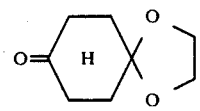

The solution was added dropwise to the above-prepared Grignard reagent at 10° to 15° C. while stirring, followed by allowing the mixture to further react at room temperature for 30 minutes. After the reaction, the reaction mixture was added to a saturated ammonium chloride aqueous solution, and the mixture was extracted with toluene. The extract was washed with water and dried, and the solvent was removed therefrom by distillation to obtain 36.1 g of a crude product containing a compound of formula:

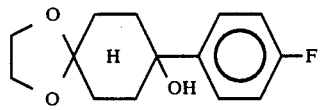

The resulting crude product was dissolved in 250 ml of toluene, and 0.24 g (0.0013 mol) of p-toluenesulfonic acid monohydrate was added thereto. The mixture was dehydrated by stirring at reflux for 2 hours, followed by cooling. The toluene layer was washed successively with a saturated sodium hydrogencarbonate aqueous solution and a saturated sodium chloride aqueous solution and dried. The toluene was removed by distillation. Recrystallization of the product from methanol gave 17.0 g (0.073 mol) (yield: 56%) of a compound of formula:

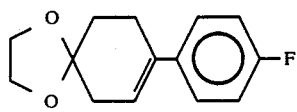

This compound was dissolved in 170 ml of ethanol, and a catalytic amount of Raney nickel was added to the solution. The mixture was stirred at room temperature at a pressure of 3.0 kg/m² or less to effect hydrogenation. After completion of the reaction, the catalyst was removed by filtration, and ethanol was removed from the filtrate by distillation to obtain 17.2 g of a crude product containing a compound of formula:

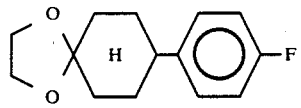

The resulting crude product was dissolved in 70 ml of toluene, and to the solution was added 50 ml of 10% sulfuric acid, followed by stirring at reflux for 4 hours. After the reaction, the reaction mixture was cooled, and the toluene layer was washed with water, dried, and distilled to removed the toluene. The residue was recrystallized from n-hexane to obtain 13.1 g (0.0682 mol) (yield: 93%) of a compound of formula:

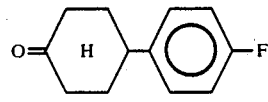

In 26 ml of anhydrous diethyl ether was dissolved 6.5 g (0.041 mol) of a compound of formula:

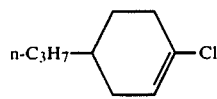

and 0.57 g (0.083 gram atom) of lithium was added to the solution, followed by stirring at reflux for 5 hours. After completion of the reaction, the reaction mixture was cooled. To the reaction mixture was added dropwise 20 ml of an anhydrous diethyl ether solution containing 7.1 g (0.037 mol) of the above-prepared compound of formula:

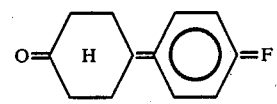

at 8° to 12° C., and the reaction was continued at room temperature for an additional period of 30 minutes. The reaction mixture was poured into cold water, and the reaction product was extracted with toluene. The extract was washed with water, dried, and distilled to remove the solvent to obtain 11.9 g of a crude product containing a compound of formula:

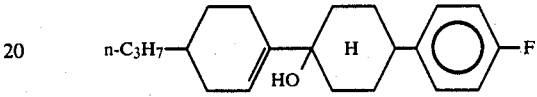

In 67 ml of acetonitrile was dissolved 17 g (0.110 mol) of sodium iodide, and 12 g (0.110 mol) of chlorotrimethylsilane was added dropwise thereto. To the resulting solution was added dropwise 35 ml of an n-hexane solution containing the above-obtained crude product at 5° to 10° C. while stirring, and the mixture was allowed to react at that temperature for 30 minutes. To the reaction mixture was added dropwise 20 g (0.130 mol) of DBU at 10° to 15° C., and the mixture was allowed to further react at room temperature (25° C.) for 19 hours while stirring. Water was added to the reaction mixture, and the reaction product was extracted with toluene. The extract was washed successivly with dilute hydrochloric acid, a saturated aqueous solution of acid sodium sulfite, a saturated sodium hydrogencarbonate aqueous solution, and a saturated sodium chloride aqueous solution, and dried. The solvent was removed from the extract by distillation to obtain a crude reaction product.

The crude product was dissolved in 50 ml of toluene, and 0.10 g (0.00053 mol) of p-toluenesulfonic acid monohydrate was added thereto. The mixture was subjected to isomerization reaction by stirring at reflux for 8 hours. After cooling, the toluene layer was washed successively with a saturated sodium hydrogencarbonate aqueous solution and a saturated sodium chloride aqueous solution and dried. Removal of the toluene by distillation gave a crude reaction product. The crude product was subjected to silica gel column chromatography and then recrystallized from ethanol to obtain 6.4 g (0.021 mol) (yield: 57%) of a mixture consisting of two compounds having formulae shown below. The mixture exhibited a nematic phase at a temperature between 54° C. and 96° C.

The mixture was subjected to high-performance liquid chromatography, and each of the searated compounds was recrystallized from ethanol to obtain the following compounds.

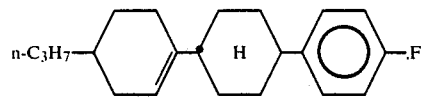

Transition temperature:

-continued

56° C. (C ⟶ N)
97° C. (N ⇌ I)

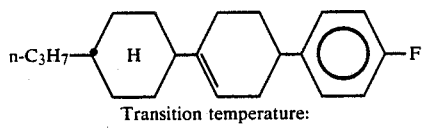

Transition temperature:

45° C. (C ⟶ N)
91° C. (N ⇌ I)

EXAMPLE 6

Two compounds of formulae shown below were obtained in the same manner as in Example 5, except for using 5.9 g (0.041 mol) of a compound of formula:

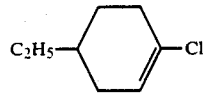

in place of the compound of formula:

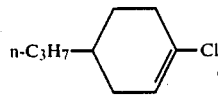

as used in Example 5.

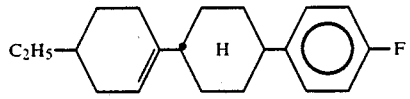

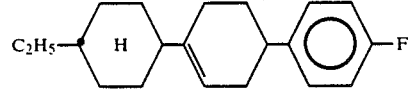

The 1:1 mixture of these two compounds showed a nematic phase at a temperature between 42° C. and 62° C.

EXAMPLE 7

Two compounds of formulae shown below were obtained in the same manner as in Example 5, except for using 7.1 g (0.041 mol) of a compound of formula:

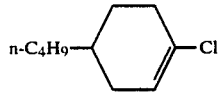

in place of the compound of formula:

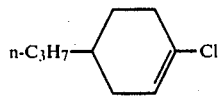

as used in Example 5.

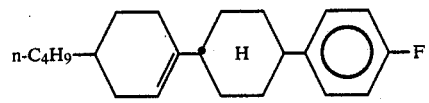

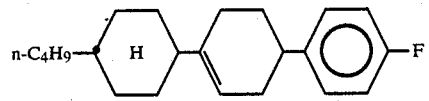

The 1:1 mixture of these two compounds showed a nematic phase at a temperature between 42° C. and 91°.

EXAMPLE 8

A mixture of two compounds of formulae shown below was obtained in the same manner as in Example 5, except for using 32.2 g (0.167 mol) of 3,4-difluorobromobenzene in place of the p-bromofluorobenzene (total yield: 36%).

The resulting mixture exhibited a nematic phase at a temperature between 19° C. and 57° C. and had a Δn of 0.076, a Δε of 5.3, and a threshold voltage of 1.93 V as measured at room temperature.

The mixture was subjected to high performance liquid chromatography, and each of the thus separated compounds was recrystallized from ethanol to obtain the following compounds.

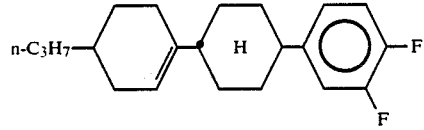

Transition temperature:

23° C. (C ⟶ N)
59° C. (N ⇌ I)

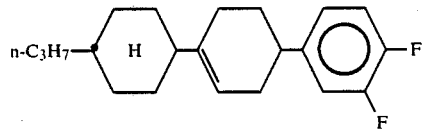

Transition temperature:

23° C. (C ⟶ N)
55° C. (N ⇌ I)

and with reference to specific embodiments thereof, it will be apparent to one skilled in the art that various changes and modifications can be made therein without departing from the spirit and scope thereof.

The compound of formula (II) according to the present invention is useful as a raw material for synthesizing compounds such as a compound of formula (I-a) having cyclohexylcyclohexens ring or a compound having dicyclohexane ring.

While the invention has been described in detail and with reference to specific embodiment thereof, it will be apparent to one skilled in the art that various changes and modifications can be made therein without departing from the spirit and scope thereof.

What is claimed is:

1. A compound represented by formula (I):

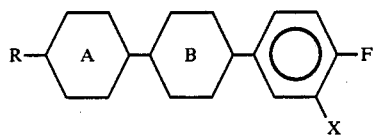
(I)

wherein R represents a straight chain alkyl group having from 1 to 9 carbon atoms;

represents

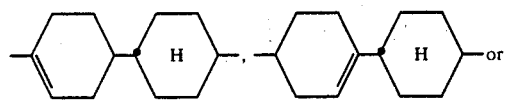

represents a hydrogen atom or a fluorine atom; and

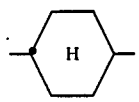

has a trans (equatorial-equatorial) configuration.

2. A compound according to claim 1, wherein

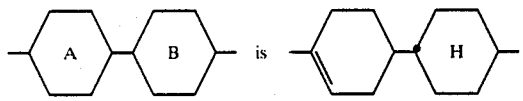

3. A compound according to claim 2, wherein X is a hydrogen atom.

4. A compound according to claim 2, wherein X is a fluorine atom.

5. A compound according to claim 1, wherein

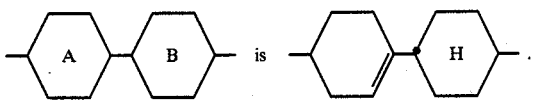

6. A compound according to claim 5, wherein X is a hydrogen atom.

7. A compound according to claim 5, wherein X is a fluorine atom.

8. A compound according to claim 1, wherein

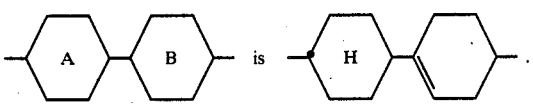

9. A compound according to claim 8, wherein X is a hydrogen atom.

10. A compound according to claim 8, wherein X is a fluorine atom.

11. A compound according to claim 3, wherein R is an n-propyl group.

12. A compound according to claim 4, wherein R is an n-propyl group.

13. A compound according to claim 4, wherein R is an n-pentyl group.

14. A compound according to claim 6, wherein R is an ethyl group.

15. A compound according to claim 6, wherein R is an n-propyl group.

16. A compound according to claim 6, wherein R is an n-butyl group.

17. A compound according to claim 7, wherein R is an n-propyl group.

18. A compound according to claim 9, wherein R is an ethyl group.

19. A compound according to claim 9, wherein R is an n-propyl group.

20. A compound according to claim 9, wherein R is an n-butyl group.

21. A compound according to claim 10, wherein R is an n-propyl group.

* * * * *